(12) United States Patent
St Pierre et al.

(10) Patent No.: US 10,285,639 B2
(45) Date of Patent: May 14, 2019

(54) METHOD AND APPARATUS FOR ESTIMATING FAT

(71) Applicant: RESONANCE HEALTH ANALYSIS SERVICES PTY LTD, Claremont, Western Australia (AU)

(72) Inventors: Timothy Guy St Pierre, Beaconsfield (AU); Sander Jonathan Bangma, Thornlie (AU); Michael J. House, Mount Lawley (AU)

(73) Assignee: Resonance Health Analysis Services Pty Ltd, Claremont, Western Australia (AU)

(*) Notice: Subject to any disclaimer, the term of this patent is extended or adjusted under 35 U.S.C. 154(b) by 220 days.

(21) Appl. No.: 14/362,792

(22) PCT Filed: Dec. 10, 2012

(86) PCT No.: PCT/AU2012/001510
§ 371 (c)(1),
(2) Date: Jun. 4, 2014

(87) PCT Pub. No.: WO2013/082677
PCT Pub. Date: Jun. 13, 2013

(65) Prior Publication Data
US 2014/0336496 A1  Nov. 13, 2014

(30) Foreign Application Priority Data

Dec. 8, 2011 (AU) .................. 2011905116

(51) Int. Cl.
*A61B 5/00* (2006.01)
*A61B 5/055* (2006.01)
(Continued)

(52) U.S. Cl.
CPC ............ *A61B 5/4872* (2013.01); *A61B 5/055* (2013.01); *A61B 5/4244* (2013.01);
(Continued)

(58) Field of Classification Search
None
See application file for complete search history.

(56) References Cited

U.S. PATENT DOCUMENTS

| 5,909,119 A | 6/1999 | Zhang et al. |
| 7,592,810 B2 | 9/2009 | Reeder et al. |

(Continued)

OTHER PUBLICATIONS

International Search Report for PCT/AU2012/001510, dated Mar. 4, 2013; ISA/AU.

(Continued)

*Primary Examiner* — Rajeev P Siripurapu
(74) *Attorney, Agent, or Firm* — Suzannah K. Sundby, Esq.; Canady + Lortz LLP

(57) ABSTRACT

Disclosed herein are methods, non-transitory computer-readable medium, and systems for determining an estimate of fat within a volume of a subject by determining a parameter α from the signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time; and determining a fat volume fraction, f, from the parameter α.

16 Claims, 12 Drawing Sheets

(51) Int. Cl.
*G01R 33/48* (2006.01)
*G01R 33/56* (2006.01)
*G01R 33/565* (2006.01)

(52) U.S. Cl.
CPC ....... *G01R 33/4828* (2013.01); *G01R 33/565* (2013.01); *G01R 33/5608* (2013.01)

(56) References Cited

U.S. PATENT DOCUMENTS

| | | | |
|---|---|---|---|
| 8,824,766 B2* | 9/2014 | Bashir | G06T 7/0012 600/410 |
| 2003/0055329 A1* | 3/2003 | Zur | G01R 33/5613 600/410 |
| 2005/0215882 A1* | 9/2005 | Chenevert | A61B 5/055 600/410 |
| 2007/0225591 A1* | 9/2007 | Derbyshire | G01R 33/483 600/410 |
| 2009/0112081 A1 | 4/2009 | Yu et al. | |
| 2011/0096974 A1 | 4/2011 | Gilson | |

OTHER PUBLICATIONS

Cassidy, F. et al. 'Fatty Liver Disease: MR Imaging Techniques for the Detection and Quantification of Liver Steatosis,' Radiographics, 2009, vol. 29(1), pp. 231-260 pp. 247-258, equations and Figs. 12-25, Appendix.

* cited by examiner

METHOD AND APPARATUS FOR ESTIMATING FAT

FIELD OF THE INVENTION

The present invention relates to a method and apparatus for estimating fat in tissue, particularly fat in the human liver. The present invention also relates to a computer program and system for implementing the method of estimating fat as well as to computer readable media carrying such a program. The present invention also provides a method of processing MRI derived images to estimate fat and a method of remotely diagnosing disorders related to unsatisfactory fat levels.

BACKGROUND TO THE INVENTION

The use of magnetic resonance imaging (MRI) and spectroscopy are well-known techniques for imaging tissue and particularly human tissue for the purpose of detecting lesions, cancers and other abnormalities.

The human liver is one organ that can be assessed using MRI. A condition of the liver known as fatty liver disease can lead to an increased risk of cancer, cardiovascular death, and cirrhosis and to reduced effectiveness of anti-viral treatments and is also implicated in the development of diabetes. Currently, histopathologists assess liver fat through visual estimation of the fat content in a liver biopsy specimen. The histopathologist carries out an estimation of the percentage of hepatocytes containing intracellular fat vacuoles and grades the sample on a scale from 0 to 3 or on a continuous scale from 0% to 100%. However, a visual estimation is, by its very nature, subjective and can be potentially unrepresentative of the whole liver. Furthermore, the process is invasive as it requires a biopsy. The accumulation of fat in tissue is often referred to as steatosis.

In terms of methods for quantifying fat in the liver, a number of MRI based techniques exist but these techniques often require complex image processing and suffer from sub-optimal sensitivity and specificity.

With the above in mind, there is a need for improved non-invasive methods for quantifying fat, i.e. steatosis, in organs such as the liver and other organs that are impacted by non-ideal fat levels.

SUMMARY OF THE INVENTION

According to an aspect of the present invention there is provided a method for determining an estimate of fat within a volume of a subject utilizing a magnetic resonance image scanner to measure signal intensities emitted from protons in the volume of the subject in response to excitation from an RF pulse; the method comprising the steps of:
   a) acquiring signal intensities of at least three echo signals emitted from a region of the volume of a subject imaged by the magnetic resonance image scanner in response to the applied RF pulse, wherein the three echo signals are taken at a first opposing-phase echo time, a second opposing-phase echo time and an in-phase echo time;
   b) determining a parameter $\alpha$ from the signal intensities; and
   c) determining a fat volume fraction, f, from the parameter $\alpha$.

According to another aspect of the present invention there is provided a magnetic resonance imaging device for determining an estimate of fat within a volume of a subject, the magnetic resonance imaging device being operable to:
   a) acquire signal intensities of at least three echo signals emitted from a region of the volume of a subject imaged by the magnetic resonance image scanner in response to an applied RF pulse, wherein the three echo signals are taken at a first opposing-phase echo time, a second opposing-phase echo time and an in-phase echo time;
   b) determine a parameter $\alpha$ from the signal intensities; and
   c) determine a fat volume fraction, f, from the parameter $\alpha$.

According to another aspect of the present invention, there is provided a computer program for instructing a computing device to determine an estimate of fat within a volume of a subject by determining a parameter $\alpha$ from signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time; and the computer program further instructs the computing device to determine a fat volume fraction from the parameter $\alpha$.

According to another aspect of the present invention there is provided an electromagnetic signal carrying computer-readable instructions for instructing a computing device to determine an estimate of fat within a volume of a subject, the computer-readable instructions being operable to: instruct the computing device to determine a parameter $\alpha$ from signal intensities of at least three echo signals received by the computing device, and emitted from a region of the volume of a subject imaged by a magnetic resonance image scanner in response to an applied RF pulse, wherein the three echo signals are taken at a first opposing-phase echo time, a second opposing-phase echo time and an in-phase echo time; and to further instruct the computing device to determine a fat volume fraction from the parameter $\alpha$.

According to another aspect of the present invention, there is provided an electromagnetic signal carrying a data file comprising information relating to a fat volume fraction determined by a computing device operable to receive signal intensities of at least three echo signals received by the computing device, and emitted from a region of the volume of a subject imaged by a magnetic resonance image scanner in response to an applied RF pulse, wherein the three echo signals are taken at a first opposing-phase echo time, a second opposing-phase echo time and an in-phase echo time; and the fat volume fraction is determined from the parameter $\alpha$ According to another aspect of the present invention there is provided a computer system comprising: a processor, and a non-transitory, tangible, program storage medium, readable by the computer system and embodying a program of instructions executable by the processor to perform steps for determining an estimate of fat within a volume of a subject, the steps including: determining a parameter $\alpha$ from signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time; and the program of instructions are further executable by the processor to determine a fat volume fraction from the parameter $\alpha$.

According to another aspect of the present invention there is provided a system for determining a estimate of fat within a volume of a subject, comprising: a magnetic resonance imaging scanner for acquiring signal intensities of at least three echo signals emitted from a region of the volume of a subject imaged by the magnetic resonance image scanner in response to an applied RF pulse, wherein the three echo signals are taken at a first opposing-phase echo time, a second opposing-phase echo time and an in-phase echo time; and a computing device for determining a parameter α from the signal intensities of the at least three echo signals; and for determining a fat volume fraction from the parameter α.

According to another aspect of the present invention there is provided a method for diagnosing a disorder associated with an unsatisfactory fat level in a subject, the method comprising the steps of:
a) using signal intensities of at least three echo signals emitted from a region of the volume of a subject in response to an applied RF pulse using a magnetic resonance imaging scanner, wherein the three echo signals are taken at a first opposing-phase echo time, a second opposing-phase echo time and an in-phase echo time, to determine a parameter α from the signal intensities of the at least three echo signals, and then a fat volume fraction from the parameter α; and
b) using the determined fat volume fraction to diagnose the disorder.

According to another aspect of the present invention there is provided a method for determining an estimate of fat within a volume of a subject comprising the steps of:
a) determining a parameter α from the signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time; and
b) determining a fat volume fraction, f, from the parameter α.

According to another aspect of the present invention there is provided a method of processing MRI derived images to determine an estimate of fat within a volume of a subject comprising the steps of:
a) determining a parameter α from the signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time; and
b) determining a fat volume fraction, f, from the parameter α.

The present invention provides for a simple MRI method and device that is a useful non-invasive tool for diagnosing and quantifying liver fat across a range of liver diseases with high sensitivity and specificity at all grades of steatosis. The present invention also provides for a method of processing MRI derived images for diagnosing and quantifying liver fat across a range of liver diseases with high sensitivity and specificity at all grades of steatosis.

DETAILED DESCRIPTION OF THE INVENTION

Figure 1:
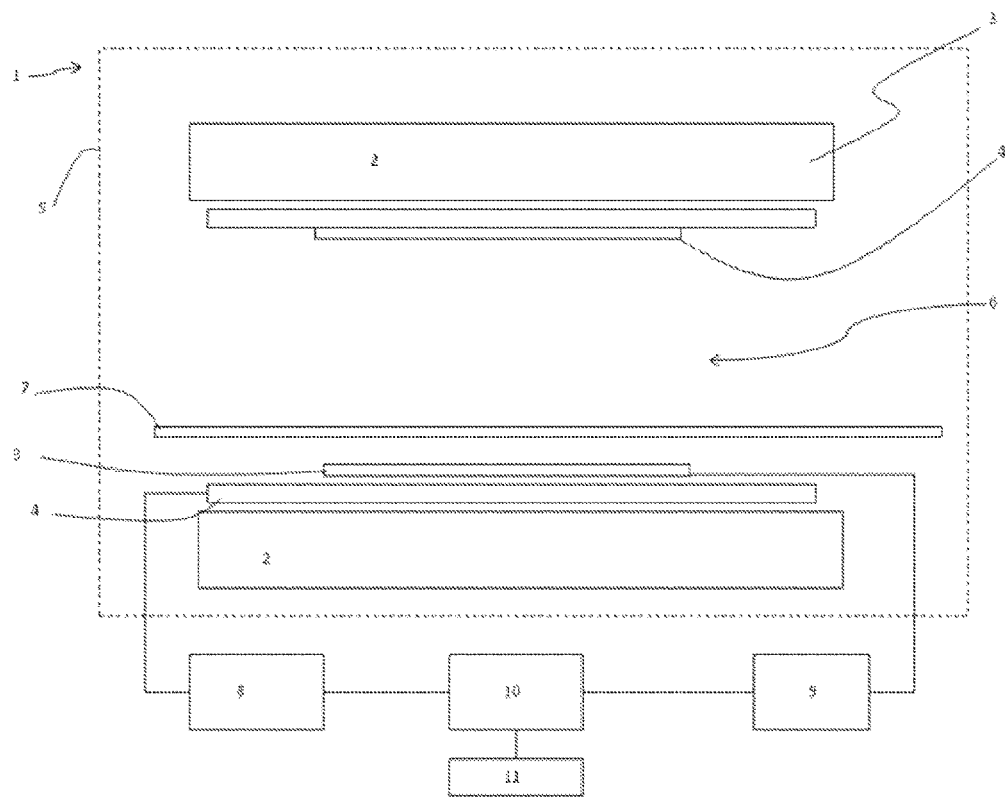
FIG. 1 is a schematic block diagram showing the components of an MRI scanner for use with the present invention.

According to one aspect of the present invention there is provided a method for determining an estimate of fat within a volume of a subject comprising the steps of:
a) determining a parameter α from the signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time; and
b) determining a fat volume fraction, f, from the parameter α.

Preferably, the fat volume fraction, f, and the value of α are related by a non-linear relationship.

Preferably, the non-linear relationship is a monotonically increasing concave function.

Preferably, the fat volume fraction, f, is determined by equation (3):

$$\alpha = \frac{kf}{(1+kf-f)}$$

Preferably, the value of k is selected to optimize the rate of change of α with respect to the fat volume fraction.

Preferably, k is greater than 1. Preferably, k is greater than 1 and less than or equal to 10. Preferably, k is 2-6, 2-4, 3-5, 2.5-3.5, 3.1-3.5 or 3.2-3.4. Preferably, k is between 3 and 4, and more preferably is 2.5, 2.6. 2.7, 2.8, 2.9, 3, 3.1, 3.2, 3.3, 3.4 or 3.5.

Preferably, the signal intensities are acquired using a flip angle of 10°-90°, 20°-80°, 30°-70°, 40°-70°, 50°-70°, 60°-70°, or 70°-90°. Even more preferably, the flip angle is 70°, 80° or 90°.

Preferably, the parameter α is determined by means of equation (1):

$$\alpha = \frac{IP - OP1\left[\exp\left(\frac{TE1-TE2}{T2^*}\right)\right]}{2IP}$$

where T2* is determined according to equation (2):

$$T2^* = \frac{(TE3-TE1)}{\ln\left(\frac{OP1}{OP2}\right)}$$

and where TE1 is the first opposing-phase echo time, TE2 the in-phase echo time, TE3 the second opposing-phase echo time, OP1 and OP2 are the signal intensities measured at the first and second opposing-phase echo times, TE1 and TE3, and IP is the signal intensity measured at the in-phase echo time.

Even more preferably, the method for determining an estimate of fat within a volume of a subject accounts for background noise. Thus, the present invention also provides a method for determining an estimate of fat within a volume of a subject comprising the steps of:

a) determining a parameter α from the signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time and wherein the signal is corrected for the presence of background noise; and
b) determining a fat volume fraction, f, from the parameter α.

Preferably, the signal intensities are corrected for background noise by determining the parameter α by means of equation (1'):

$$\alpha = \frac{IP_T - OP1_T\left[\exp\left(\frac{TE1-TE2}{T2^*}\right)\right]}{2IP_T}$$

where T2* is determined according to equation (2'):

$$T2^* = \frac{(TE3-TE1)}{\ln\left(\frac{OP1_T}{OP2_T}\right)}$$

and $OP1_T$, $IP_T$ and $OP2_T$ are the true signal intensities in the absence of noise in regions-of-interest in the first opposed-phase, in-phase and second opposed-phase images. The true signal intensity, $S_T$, is determined as follows:

$$S_T = \sqrt{S_M^2 - N_M^2}$$

where:
$S_T$ is the true signal intensity within the region-of-interest corrected for background noise levels, $S_M$ is the measured signal intensity within the region-of-interest in the magnitude MR image and $N_M$ is the measurement of the background noise levels in the magnitude MR image in an area free of image artefacts and structured noise.

Preferably the background noise signal intensities are subtracted in quadrature.

The background noise intensity level that is used to calculate the true signal intensity can be determined in a number of ways. These include the statistical mean of the signal intensities within the background region-of-interest of the magnitude image or the statistical mean plus an offset such as one standard deviation of the background noise intensity levels. Alternatively, the background noise intensity level can be determined by fitting a probability density function to the distribution of the signal intensities within the background region-of-interest. Examples of such probability density functions are; a Gaussian distribution, a Rician distribution or a Poisson distribution. The mean of the fitted probability density function can be used as an estimate of the background noise intensity level or the mean plus an offset such as one standard deviation of the fitted probability density function.

Preferably, the parameter α is determined as the average over three consecutive axial image slices along an axis.

Preferably, the volume of the subject comprises an organ, or part of an organ, such a liver, kidney, and pancreas.

According to another aspect of the present invention there is provided a method for determining an estimate of fat within a volume of a subject utilizing a magnetic resonance image scanner to measure signal intensities emitted from protons in the volume of the subject in response to excitation from an RF pulse; the method comprising the steps of:

a) acquiring signal intensities of at least three echo signals emitted from a region of the volume of a subject imaged by the magnetic resonance image scanner in response to the applied RF pulse, wherein the three echo signals are taken at a first opposing-phase echo time, a second opposing-phase echo time and an in-phase echo time;
b) determining a parameter α from the signal intensities; and
c) determining a fat volume fraction, f, from the parameter α.

Preferably at least two of the method steps are carried out at different locations.

For example, the signal intensities may be acquired at one location and the remaining steps may be carried out at second location.

The present invention can utilise a known MRI scanner such as the Siemens 1.5 T Avanto scanner available from Siemens Medical Systems, Erlangen, Germany, although any other suitable scanner could be used.

According to another aspect of the present invention there is provided a magnetic resonance imaging device for determining an estimate of fat within a volume of a subject, the magnetic resonance imaging device being operable to:

a) acquire signal intensities of at least three echo signals emitted from a region of the volume of a subject imaged by the magnetic resonance image scanner in response to an applied RF pulse, wherein the three echo signals are taken at a first opposing-phase echo time, a second opposing-phase echo time and an in-phase echo time;

b) determine a parameter $\alpha$ from the signal intensities; and c) determine a fat volume fraction, f, from the parameter $\alpha$.

According to another aspect of the present invention, there is provided a computer program for instructing a computing device to determine an estimate of fat within a volume of a subject by determining a parameter $\alpha$ from signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time; and the computer program further instructs the computing device to determine a fat volume fraction from the parameter $\alpha$.

According to another aspect of the present invention there is provided an electromagnetic signal carrying computer-readable instructions for instructing a computing device to determine an estimate of fat within a volume of a subject, the computer-readable instructions being operable to: instruct the computing device to determine a parameter $\alpha$ from signal intensities of at least three echo signals received by the computing device, and emitted from a region of the volume of a subject imaged by a magnetic resonance image scanner in response to an applied RF pulse, wherein the three echo signals are taken at a first opposing-phase echo time, a second opposing-phase echo time and an in-phase echo time; and to further instruct the computing device to determine a fat volume fraction from the parameter $\alpha$.

According to another aspect of the present invention, there is provided an electromagnetic signal carrying a data file comprising information relating to a fat volume fraction determined by a computing device operable to receive signal intensities of at least three echo signals received by the computing device, and emitted from a region of the volume of a subject imaged by a magnetic resonance image scanner in response to an applied RF pulse, wherein the three echo signals are taken at a first opposing-phase echo time, a second opposing-phase echo time and an in-phase echo time; and the fat volume fraction is determined from the parameter $\alpha$.

According to another aspect of the present invention there is provided a computer system comprising: a processor, and a non-transitory, tangible, program storage medium, readable by the computer system and embodying a program of instructions executable by the processor to perform steps for determining an estimate of fat within a volume of a subject, the steps including: determining a parameter $\alpha$ from signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase echo time; and the program of instructions are further executable by the processor to determine a fat volume fraction from the parameter $\alpha$.

According to another aspect of the present invention there is provided a system for determining a estimate of fat within a volume of a subject, comprising: a magnetic resonance imaging scanner for acquiring signal intensities of at least three echo signals emitted from a region of the volume of a subject imaged by the magnetic resonance image scanner in response to an applied RF pulse, wherein the three echo signals are taken at a first opposing-phase echo time, a second opposing-phase echo time and an in-phase echo time; and a computing device for determining a parameter $\alpha$ from the signal intensities of the at least three echo signals; and for determining a fat volume fraction from the parameter $\alpha$.

According to another aspect of the present invention there is provided a method for diagnosing a disorder associated with an unsatisfactory fat level in a subject, the method comprising the steps of:

a) using signal intensities of at least three echo signals emitted from a region of the volume of a subject in response to an applied RF pulse using a magnetic resonance imaging scanner, wherein the three echo signals are taken at a first opposing-phase echo time, a second opposing-phase echo time and an in-phase echo time, to determine a parameter $\alpha$ from the signal intensities of the at least three echo signals, and then a fat volume fraction from the parameter $\alpha$; and b) using the determined fat volume fraction to diagnose the disorder.

For the purposes of the present invention the term "unsatisfactory fat level" includes non-normal fat levels and any other fat levels that may result in deleterious health consequences for a subject.

Preferably the method further comprises the step of acquiring the signal intensities.

According to another aspect of the present invention there is provided a method of processing MRI derived images to determine an estimate of fat within a volume of a subject comprising the steps of:

a) determining a parameter $\alpha$ from the signal intensities of at least three echo signals emitted from a region of the volume of a subject imaged by a magnetic resonance image scanner in response to an applied RF pulse, wherein the three echo signals are taken at a first opposing-phase echo time, a second opposing-phase echo time and an in-phase; and b) determining a fat volume fraction, f, from the parameter $\alpha$.

Preferred aspects of the present invention will now be described with reference to FIGS. 1 and 2, that in no way limits the generality of the preceding paragraphs and where FIG. 1 illustrates schematically the functional components of an MRI scanner. Briefly, an MRI scanner 1 comprises: a magnet 2 which provides a static magnetic field; gradient coils 3 which provide localised magnetic fields along three orthogonal directions to impose spatial gradients on the static magnetic field to spatially distribute the static magnetic field; and a radio frequency (RF) coil 4 to provide RF pulses to excite nuclei, and particularly hydrogen nuclei, within the tissue to be imaged. The magnet 2, gradient coils 3 and RF coil 4 are housed within a housing 5 which shields these components, and which includes an aperture 6 into which a patient is placed. A patient table 7 is provided for this purpose and which moves in and out of the housing 5 so that the patient can be moved in and out of the scanner 1. The gradient field enables spatial information for the image to be adduced.

The gradient coils 3 and RF coil 4 are controlled by relevant controllers 8, 9.

The magnet 2 provides the static magnetic field which magnetises hydrogen nuclei (which comprise a single proton) that are within the static magnetic field.

The hydrogen nuclei/protons are then excited by the imposition of a magnetic pulse from the RF coil 4 orthogonal to the static magnetic field and at a resonant frequency known as the Larmor frequency. After excitation by the pulse from the RF coil 4, the hydrogen nuclei emit a signal—known as the free induction decay (FID).

A second MRI signal called the echo signal is also emitted after application of a magnetic field gradient pulse. The FID signal and the echo signals are detected and transmitted to a processor 10 which analyses the received signal using Fourier Transform Analysis to produce an image of the excited region of the patient's body. The image(s) can be displayed on a display 11 or printed out. Multiple images can be sequentially taken along the longitudinal z-axis (or any other direction) which can be used to build up a three-dimensional view of the patient's body which can then be subsequently analysed by the clinician, for example by a radiologist.

The use, operation and function of MRI scanners for the imaging and analysis of tissue is well known to persons skilled in the art and need not be described in any further detail herein except as is relevant to the present invention.

While certain parameters are preset by the manufacturer (such as the strength of the static magnetic field), other parameters can be set by the operator as required for the imaging purposes. Such parameters include:

The repetition time TR—being the interval between RF excitation pulses;

The echo time TE—being the time at which echo signals are set to be detected;

The flip angle—being the angle to which the magnetisation is to be flipped; and

Bandwidth—being the frequency range of the measured signal in the Fourier domain.

Other parameters that define MRI signals are the longitudinal relaxation time T1, and the Free Induction Decay (FID) transverse relaxation time constants T2 and T2*. T1, T2 and T2* are all well known in the art.

In an embodiment of the present invention, the MRI scanner 1 is set to the following parameters:

a gradient echo sequence (and in particular a spoiled gradient recalled echo sequence) with a single pulse excitation for a flip angle of $70°$;

a repetition time, TR=88 ms;

echo times TE1, TE2, and TE3 (i.e. times for detection of echo signals) of 2.38 ms, 4.76 ms, and 7.14 ms respectively; and pixel bandwidth 500 Hz;

Preferably, data is taken from three axial slices through the widest part of the liver: each axial slice having a thickness of 4 mm. The matrix may be 256×256 with a field of view of 300 mm×300 mm.

The data may be acquired in a single breath hold. This is achievable due to the use of a relatively short repetition time (TR). A shorter repetition time allows for a quick acquisition. When a limited number of slices are acquired, this also enables the data to be acquired within this repetition time. A 'partial Fourier' analysis may also be used in the signal processing to exploit some of the symmetry in the Fourier domain to speed up acquisition. The use of partial Fourier analysis is well known to persons skilled in the art and need not be described in any further detail herein.

In the present invention, it is preferred to use a 3-point Dixon method to enable any effect of T2* to be taken into account as will be described further below.

For each axial slice, a single excitation pulse can be applied by the RF coil 4 to flip the magnetisation vector by $70°$, with a rephasing produced by switching of the gradient fields. Signal intensities may be measured at the three echo times TE1, TE2 and TE3.

As is known to persons skilled in the art, the magnetisation vectors precess around the z-axis at slightly different Larmor frequencies when in fat compared to water. As the magnetisation vectors precess at different rates they will start in-phase, but will then start to precess out of phase to the point where they are $180°$ out-of-phase (i.e. in opposing phase) and then will become in-phase again and so on.

In a 3-point Dixon method, the three gradient echo signal intensities are measured for a designated region of interest (ROI) of the tissue sample—a first when the precessing magnetisation vectors are in opposing phase (OP1), a second when they are in-phase (IP) and a third again when they are in opposing phase (OP2). These echo times at which these intensities OP1, IP, OP2 are measured are designated TE1, TE2, and TE3 respectively as mentioned above.

Figure 2:
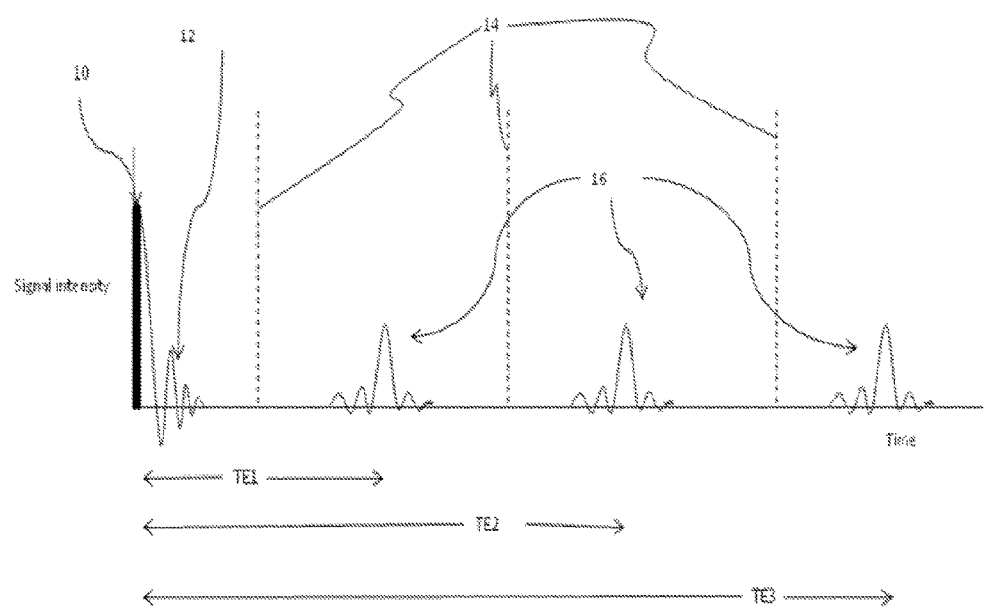
FIG. 2 is a graph showing the MRI excitation pulse and MRI signal responses for a single excitation step as in the present invention.

FIG. 2 illustrates schematically a graph showing the excitation pulse, gradient pulses and MRI signal responses for a single excitation step of the present invention—specifically the RF pulse 10, followed by the emission of an FID signal 12, the imposition of a gradient pulse 14 for rephasing and the detection of three echo pulses 16 at the three predetermined periods of time: TE1, TE2 and TE3.

For a static magnetic field of 1.5 T it can be determined that if tissue water and fat protons precess initially in-phase, they will be $180°$ out-of-phase 2.38 ms later, in-phase after another 2.38 ms and so on. It is for this reason that the echo times TE1, TE2 and TE3 are selected to be 2.38 ms, 4.76 ms and 7.14 ms.

It will be understood that different echo times can be used depending upon the Larmor frequencies used. Furthermore, the echo times are calculated based on an assumed water-fat chemical shift. Different values of chemical shift are provided in the literature and—as such—the calculated echo times may vary.

A value—$\alpha$—which derives from the image intensities in the first opposed-phase, in-phase and second opposed phase images can be calculated, using equation 1.

Preferably, the value a is completely determined by imaging parameters.

Preferably, measurements are taken for a region of interest (ROI) comprising a circular region (of approximately 30 mm diameter) in the right lobe of the liver and in an area free of vessels and artefacts (across all 3 slices and echo-times).

The signal intensities from three consecutive image slices along the z-axis can then be processed by the processor 10 of the MRI scanner 1, or using a processor of a remote computer or other computing device, and a value of a computed. Preferably, the value of $\alpha$ determined is one which is the average over three consecutive axial image slices along the z-axis.

In the present invention, the flip angle is set to a relatively high value. In the embodiment described herein the flip angle is set to $70°$, although other flip angles are envisaged. In particular, the flip angle can be selected from the range of $10°$ to $90°$.

A quantitative measure—the fat volume fraction f—being a measure of the amount of fat in a selection of tissue rather than simply a measure of the ratio of the number of protons in fat to protons in water—can be determined from α.

The use of a high flip angle provides for a good signal-to-noise ratio and increased sensitivity of α to changes in fat volume fraction by increasing k.

In this embodiment of the invention, the signal analysis and computation of α, and therefore f, for a known value of k, can be implemented within the MRI scanner 1, with output via the display 11 or any other suitable means.

Alternatively, the processing can implemented through means of a software programme stored on storage media which can be used by a computer or other suitable computing device connected directly to the MRI scanner 1 or remote therefrom.

Outputs can also be in the form of an electronic data file for processing remotely and can be transmitted, for example, using email, electronic file transfer, the Internet, or any other suitable electronic data transmission process. The electronic data file can also be stored remotely, for example, on a transportable storage media, on a remote server, or using so called 'cloud computing', for example.

In this way, the MRI scanner 1 can be used to take the requisite images which can then be transmitted to the remote computing device by means of an electronic date file for the computation of the value a, and thus the value of fat volume fraction f thereby. The computed values of fat volume fraction f can then be returned to a user at the MRI scanner 1 or to a third party elsewhere: again by electronic data file transfer.

For example, for diagnosis of a particular condition, a patient could present to a radiologist at a first location who could operate the MRI scanner 1 to take the requisite images. These could then be sent electronically (e.g. by email or via the Internet) as a data file to a second location where a remote computer or other computing device could analyse the images and compute the values of α and f and compile a report which could then be sent (again as an electronic data file) to a third location which could be a patient's physician, who would be able to carry out an appropriate diagnosis.

General

Those skilled in the art will appreciate that the invention described herein is susceptible to variations and modifications other than those specifically described. The invention includes all such variation and modifications. The invention also includes all of the steps and features referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness. None of the cited material or the information contained in that material should, however be understood to be common general knowledge.

The present invention is not to be limited in scope by any of the specific embodiments described herein. These embodiments are intended for the purpose of exemplification only. Functionally equivalent products and methods are clearly within the scope of the invention as described herein.

The invention described herein may include one or more range of values (e.g. size etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all technical terms used herein have the same meaning as commonly understood to one of ordinary skill in the art to which the invention belongs.

The present invention now will be described more fully hereinafter with reference to the Examples, in which certain preferred embodiments of the invention are shown. This invention may, however, be embodied in many different forms and should not be construed as limited to any of the embodiments set forth herein; rather, the embodiments are provided so that this disclosure will be thorough and complete, and will fully convey the scope of the invention to those skilled in the art.

EXAMPLES

Example 1—Empirical Derivation of k

The relationship between the fat volume fraction, f, and the determined value a can be defined as equation 3:

$$\alpha = \frac{kf}{(1 + kf - f)} \quad (3)$$

where k is a constant.

Equation 3 illustrates a relationship between α and the fat volume fraction, f, for a given value of k, k being dependent on flip angle, θ, repetition time, TR, and longitudinal relaxation times for fat and non-fat tissue respectively, and the ratio of the densities of protons in vesicular fat and liver tissue.

Figure 3:
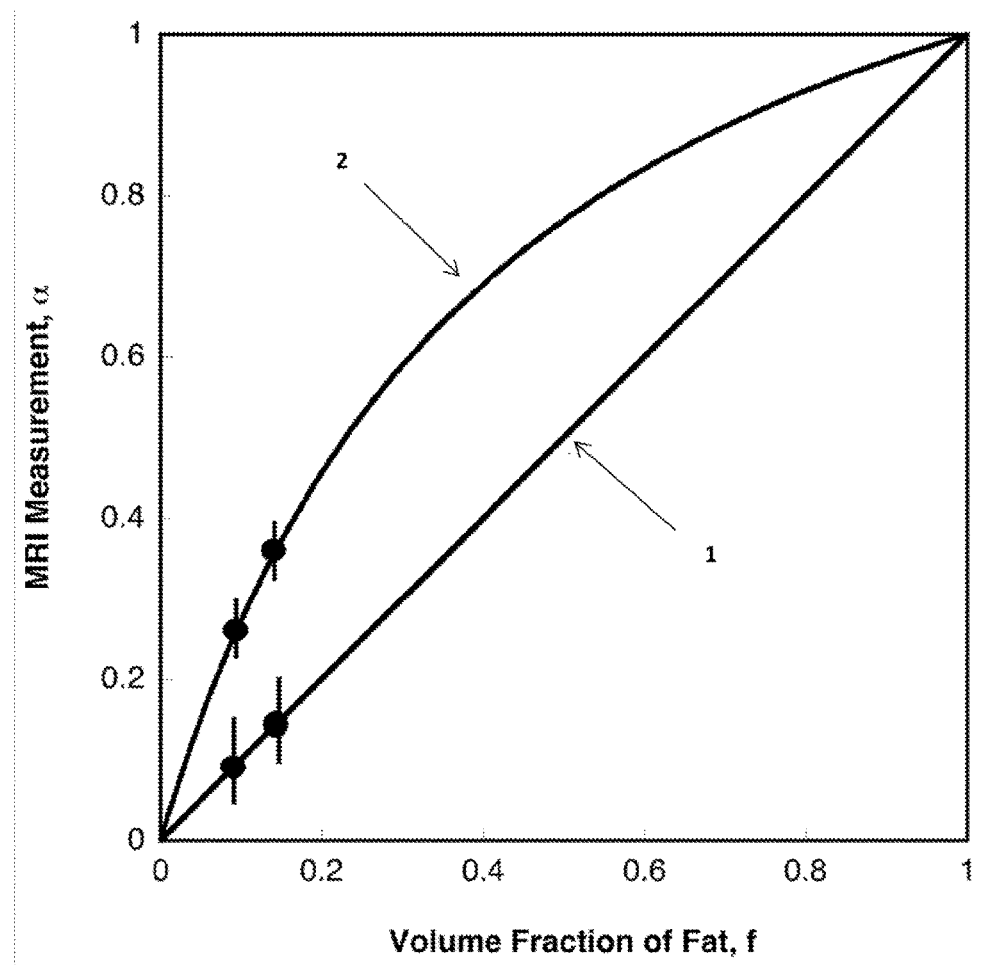
FIG. 3 is a graph of MRI derived α against determined fat volume fraction f for the present invention.

If the determined values of α from equation (3) above are plotted against fat volume fraction (f), a non-linear relationship is shown and indicated by the curve 2 in FIG. 3. Preferably, the non-linear relationship is a monotonically increasing concave function.

The form of this curve is also determined by the difference in T1 between the fat in the tissue and the water in the tissue as well as the difference in MR detectable proton density between the fat deposits and the remaining tissue. It has also been determined that the amount of curvature of this line increases with increasing flip angle—as indicated by curve 2 in FIG. 3.

This curve 2 provides a means of calibrating the relationship between α measured by the MRI scanner 1 and a fat volume fraction, f, measured from histological sections of biopsy tissue to enable MRI to non-invasively measure liver fat volume fraction—see HIST_MORPH in the examples provided below.

The value of the constant, k which—as mentioned above—can be derived empirically, is determined by experimentally estimating liver fat volumes using a measurement of percentage area of fat vacuoles in Masson trichrome stained histological sections which are assessed by computer assisted morphometric analysis, as described further below in Examples 3A and 3B. This is then used to derive the calibration curve with the algebraic formula as per equation 3 above, and that is fitted to the computed values of α. From this curve, a value of k can be determined.

Thus, for a known value of k, a quantitative value for the fat volume fraction f in a tissue can be determined from the computed value of α in accordance with the invention. Furthermore, once the fat volume fraction within a volume of the subject has been determined, then the corresponding fat volume can be derived by multiplying the fat volume fraction, f, by the volume of the subject within the measured region of interest.

Preferably, k is greater than 1, and specifically in the range greater than 1 and less than or equal to 10, and more specifically between 2 and 4. According to FIG. 10 herein k=3.32 (to two decimal places)—see the discussion in respect of FIG. 10 below.

This is different from prior attempts at improving the Dixon method which have aimed at obtaining a 1:1 linear relationship between the MRI measured quantity of a which equates to the straight line 1 in FIG. 3.

In the present invention, the difference in T1 between fat and tissue water is exploited to distort the relationship away from a linear 1:1 relationship to the non-linear relationship as indicated by the curve 2 in FIG. 3. For tissues with a limited range of fat volume fraction, f, (e.g. from 0.00 to 0.40) the sensitivity of the MRI measurement a for predicting the fraction of protons in fat is enhanced for two reasons:

1. The differential of the relationship between the MRI measurement a and the fraction of tissue protons in fat is increased i.e. the gradient of the curve 2 in FIG. 3 is greater than the gradient of line 1 in FIG. 3 over the range of interest; and
2. The random error on the MRI measurement a can be decreased owing to better signal to noise ratios in the MRI data.

As can be seen in FIG. 3, the combination of these two effects can result in a much better discrimination of small changes in the fraction of tissue protons in fat. Note that the error bars do not overlap when using curve 2 but do when using the straight line 1.

The experimental error on a measurement of a is related to the signal-to-noise ratios in the in-phase and opposed-phase images. Assuming that the absolute error Δα on a is approximately the same for all values of α, the sensitivity of α to f, will be proportional to dα/df. α will be most sensitive to small changes in fat volume fraction, f, when dα/df is maximised. Using equation 3 above, then:

$$\frac{d\alpha}{df} = \frac{k}{(1+kf-f)^2}$$

If dα/df=x, then mapping x as a function of k and f enables preferred values of k to be determined.

Figure 10:
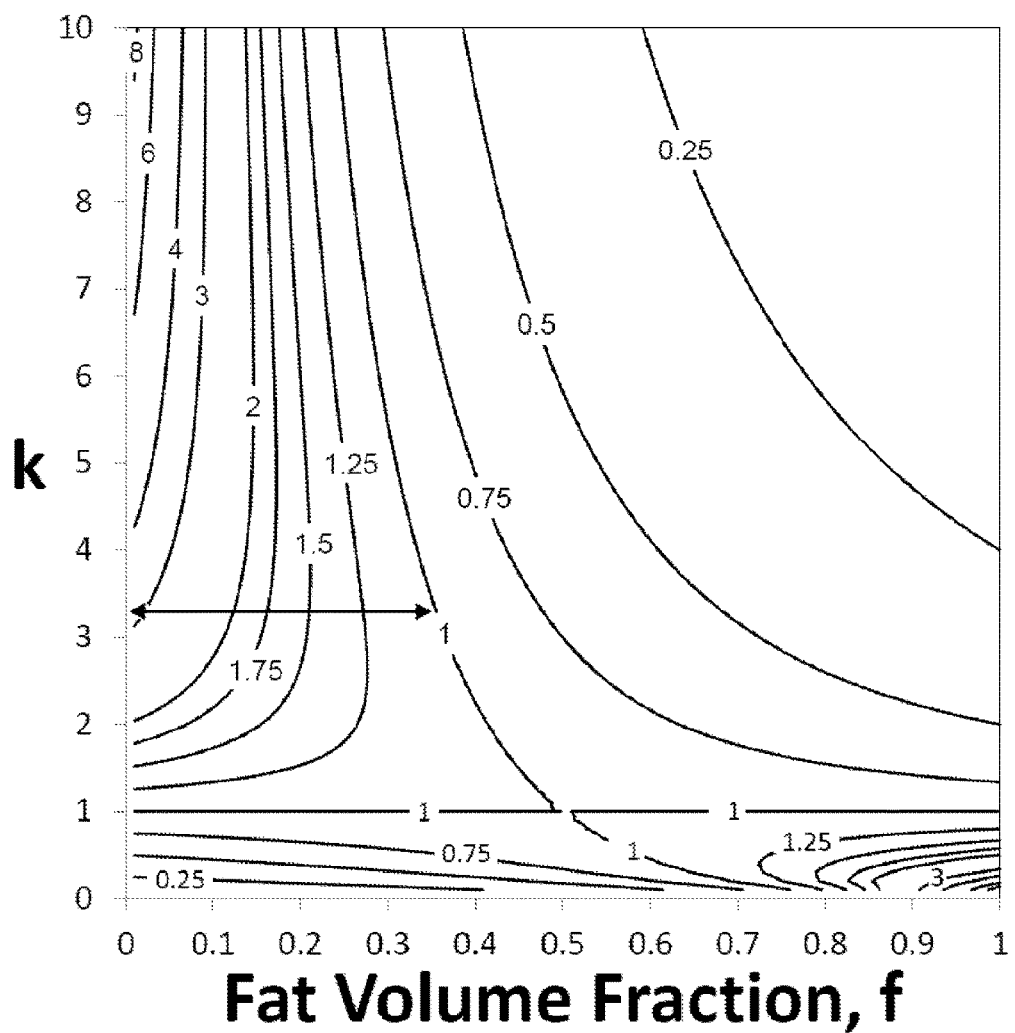
FIG. 10 is a map of the rate of change of a with fat volume fraction, f, for different values of k.

FIG. 10 shows such a mapping of x as a function of k and f. Areas where x is greater than 1 indicate measurements where there is enhanced sensitivity.

FIG. 10 shows that where k is chosen to be greater than 1, and more specifically somewhere from 2 to 10, then the measurements provide enhanced sensitivity for a limited range of fat volume fractions i.e. x is greater than 1.

It should be noted that, in clinical environments, the maximum value of fat volume fraction, f, that is usually required to be measured is 0.25 (i.e. 25% of a volume is fat) and—as such—FIG. 10 shows that these values of k mentioned above provide optimum sensitivity. With a value of k of approximately 3.32, the present invention provides cover for the range of liver fat volume fractions f up to about 0.35 (i.e. 35%) with enhanced sensitivity over the whole range. Furthermore, most clinical changes occur when f is in the range of 0 to 0.07 in which a value of k of 3.32 gives x values of 2.5 to 3.0 i.e. sensitivities 2.5 to 3.0 times greater than would be achieved with a k value of 1.

The double headed arrow in FIG. 10 indicates the part of the sensitivity map covered by the MRI method using k=3.32 that provides sensitivity enhancement. This shows that below a liver fat volume fraction, f, of about 0.35, the technique of the present invention gives enhanced sensitivity. However, above f=0.35, sensitivity would be reduced. By tracing the eye along the double-headed arrow, the sensitivity enhancement factor and how it increases as we move to lower liver fat volume fractions can be seen.

Example 2—Analytical Derivation of k

As indicated elsewhere herein, the relationship between the fat volume fraction, f, and the determined value can be defined by equation 3:

$$\alpha = \frac{kf}{(1+kf-f)} \qquad (3)$$

As also indicated the value of k is dependent on the acquisition flip angle, repetition time, longitudinal relaxation times for fat and non-fat tissue, and the ratio of the density of protons in fat to the density of protons in non-fat liver tissue.

The value of k can be derived analytically by taking this into account and expressing k as follows:

$$k = \gamma C$$

where:

$$\gamma = \frac{f_{fat}}{f_{tissue}}$$

and $$f_{fat} = \frac{\sin(\theta)[1-\exp(-TR/T_{1\,fat})]}{1-\cos(\theta)\exp(-TR/T_{1\,fat})}$$

and $$f_{tissue} = \frac{\sin(\theta)[1-\exp(-TR/T_{1\,tissue})]}{1-\cos(\theta)\exp(-TR/T_{1\,tissue})}$$

The equations for $f_{fat}$ and $f_{tissue}$ can be derived from the signal for a spoiled gradient echo image acquisition sequence, where θ is the flip angle, TR is the repetition time and $T_{1\,fat}$ and $T_{1\,tissue}$ are the longitudinal relaxation times for fat and non-fat tissue respectively.

The value for C can be derived from the ratio of the density of protons in fat to the density of protons in non-fat liver tissue. The exact chemical composition of the microvesicular fat in liver tissue is not known. However, it is known to consist of triglycerides. Preferably, linoleic acid is used as a model compound to make an estimation of the density of protons in a typical mixture of triglycerides. Linoleic ($C_{18}H_{32}O_2$) acid has a density of 0.9 g/cm3 and molar mass of 280.45 g/mol. From this information it can be deduced that the density of protons in linoleic acid is 0.103 mol/cm$^3$. To determine the density of protons in non-fat liver tissue it is assumed that all MR detectable protons in this tissue are associated with water molecules. Liver tissue on average has a wet to dry weight ratio of 3.8 and the average density of liver tissue is 1.051 g/cm$^3$. From this information it can be deduced that the density of water protons in liver tissue is 0.086 mol/cm$^3$.

Hence, the ratio of the density of protons in liver fat to the density of water protons in liver tissue (C) is estimated to be approximately 1.2.

In an embodiment of the present invention k is derived using a spoiled gradient echo sequence with the following parameters:
 a flip angle of 70°
 a repetition time of 88 ms
and using the following longitudinal relaxation times for fat and non-fat tissue:
 T1 value of fat: 145 ms
 T1 value of non-fat tissue: 570 ms
and using a ratio of the density of protons in liver fat to the density of water protons in liver tissue (C) of 1.2.

Given the above parameters the derived value for k in this embodiment is: 3.3.

Example 3A—Diagnostic Performance of a Rapid Magnetic Resonance

Imaging Method of Measuring Hepatic Steatosis
(A) Materials/Methods
Subjects

Ten healthy controls and fifty consecutive patients were prospectively enrolled for a general liver study. Informed consent was obtained from each subject included in the study and the study protocol conformed to the ethical guidelines of the 1975 Declaration of Helsinki as reflected in a priori approval by the Fremantle Hospital Human Research Ethics Committee. The patients were recruited from the hepatology outpatient clinics at Fremantle and Sir Charles Gairdner Hospitals, Western Australia. The patient inclusion criteria were: age between 18 and 65 years, for patients without cirrhosis the availability of a liver biopsy obtained within 12 months of MRI, alcohol consumption less than 20 grams per day for men and less than 10 grams per day for women, written informed consent. Control subjects were not biopsied and required a body mass index (BMI) less than 25 and no history of liver disease. The exclusion criteria were: contraindications for MRI, ischemic heart disease as determined by history or abnormal ECG, pregnancy or lactation, malignancy (excluding basal cell or squamous cell skin cancers). Two patients were excluded because an incorrect MRI sequence was used to acquire data and one cirrhotic case did not have a biopsy sample, leaving 47 patients in the final cohort. The details of the cohorts are shown in Table 1.

TABLE 1

Study Cohort Details

| Characteristics | Patients (N = 47) | Controls (N = 10) | p |
|---|---|---|---|
| Gender (Male/Female) | 25/22 | 7/3 | 0.487 |
| Age (years) | 50.7 ± 14.3 | 35.6 ± 8.7 | 0.002 |
| LIC (mg/g) | 1.16 ± 0.74 | 1.09 ± 0.44 | 0.775 |
| BMI (kg/m$^2$) | 28.38 ± 5.23 | 22.55 ± 1.77 | 0.001 |
| Biopsy-MRI Interval (days) | 155.5 ± 282 | | |
| METAVIR 0 | 13 | | |

TABLE 1-continued

Study Cohort Details

| Characteristics | Patients (N = 47) | Controls (N = 10) | p |
|---|---|---|---|
| METAVIR 1 | 13 | | |
| METAVIR 2 | 5 | | |
| METAVIR 3 | 9 | | |
| METAVIR 4 | 7 | | |
| Diagnosis | | | |
| AIH | 3 | | |
| CIRR | 2 | | |
| HBV-HCV | 13 | | |
| HEM | 2 | | |
| NAFLD-NASH | 18 | | |
| PSC | 4 | | |
| UNKNOWN | 6 | | |

Abbreviations:
AIH—autoimmune hepatitis,
CIRR—cirrhosis,
HBV-HCV—viral hepatitis B/C,
HEM—haemochromatosis,
LIC—liver iron concentration,
NAFLD-NASH—non-alcoholic fatty liver disease/non-alcoholic steatohepatitis,
PSC—primary schlerosing cholangitis Liver Histology and Quantification of Liver Fat The patients underwent percutaneous liver biopsy with ultrasound guidance as part of their routine clinical management. Each liver biopsy specimen was prepared for histological examination before being retrospectively reviewed by an experienced hepatopathologist blinded to the patient's identity and MRI data. The percentage of hepatocytes containing fat was visually estimated between 0% and 100% (HIS-VIS).

Computer Assisted Morphometric Image Analysis of Liver Fat Area

Figure 4:
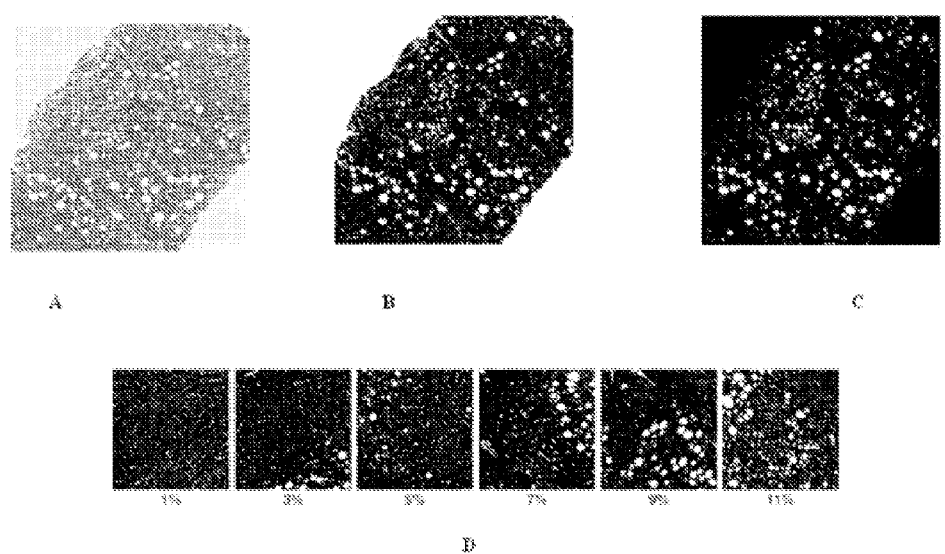
FIG. 4A is a histology image of a patient for an example of the present invention.
FIG. 4B is a binary image of FIG. 4A after application of threshold.
FIG. 4C is the mask showing fat vacuoles after application of size and structural criteria of the image of FIG. 4A.
FIG. 4D are examples of binary histology images (like that of FIG. 4B) for a range of fat percentage areas.

The percentage area of fat vacuoles in Masson trichrome stained histological sections was assessed by computer assisted morphometric analysis. The percentage area of fat in a tissue biopsy specimen is equivalent to the volume fraction of fat in the tissue. Biopsy histological section slides were scanned in colour at high resolution using an Aperio Scanscope XT (Aperio Technologies, Inc., California, USA) automated slide scanner and ImageScope software. Using ImageJ 1.42 (NIH, USA) software, the fat vacuoles were automatically identified and areas measured in a multi-stage process using thresholding, size, and circularity criteria. Fat vacuoles, holes, tears or vessels in the biopsy section appear as high intensity (white) areas (FIG. 4A). These high intensity regions were automatically segmented by applying a threshold intensity of 220 (out of 256) on the green image band, which on inspection provided the best contrast between fat vacuoles and liver parenchyma. The threshold image was converted into a binary image such that the fat vacuoles and any other high intensity regions were given a value of 255 and non-fat tissue a value of 0 (FIG. 4B). The fat vacuoles were then automatically identified and delineated using the Analyze Particles tool in ImageJ with a circularity index between 0.5 and 1 and a size threshold between 100 and 10000 pixels (equivalent to diameters from 5.6 to 56 μm). The circularity index ranges from 0 (infinitely elongated polygon) to 1 (perfect circle) and is defined as $(4\pi \times Area)/Perimeter^2$.

The criteria for thresholding intensity, size, and circularity were established by inspection of the results of different thresholds on the effective simultaneous exclusion of large vessels, ducts or other large areas of high intensity and inclusion of fat vacuoles. The analysis produced the size and circularity of each individual fat vacuole and the total area of all the fat vacuoles within the threshold ranges. To compute the total area of the biopsy sample the binary image was reversed and the Fill Holes tool used to produce a biopsy image without holes. The total area of the biopsy sample was measured and the areal fat percentage (HIS-MORPH) computed from the ratio of fat area to total tissue area.

The images in FIG. 4D have been thresholded as in FIG. 4B, but not masked (as in FIG. 4C), so as to keep the additional white spaces that are not represented in the area fat estimate, but are visible in a histology image. Each square is 500 microns across.

MRI
Data Acquisition

All MRI measurements were taken in accordance with the invention described above and made on Siemens 1.5 T Avanto scanners (Siemens Medical Systems, Erlangen, Germany) at Fremantle Hospital, St John of God Murdoch Hospital, and Hollywood Private Hospital, Western Australia. Phased-array torso coils were centred over the liver of the subjects. Data acquisition comprised an in-phase, opposed-phase spoiled gradient recalled echo sequence (TR 88 ms, TEs 2.38, 4.76, 7.14 ms, 1 excitation, flip angle 70°, bandwidth 500 Hz). Data from three axial slices, positioned through the widest part of the liver, were acquired in a single breath-hold. The slice thickness was 4 mm and the matrix was 256×256 with a field of view 300×300 mm.

Image Processing

Figure 5:
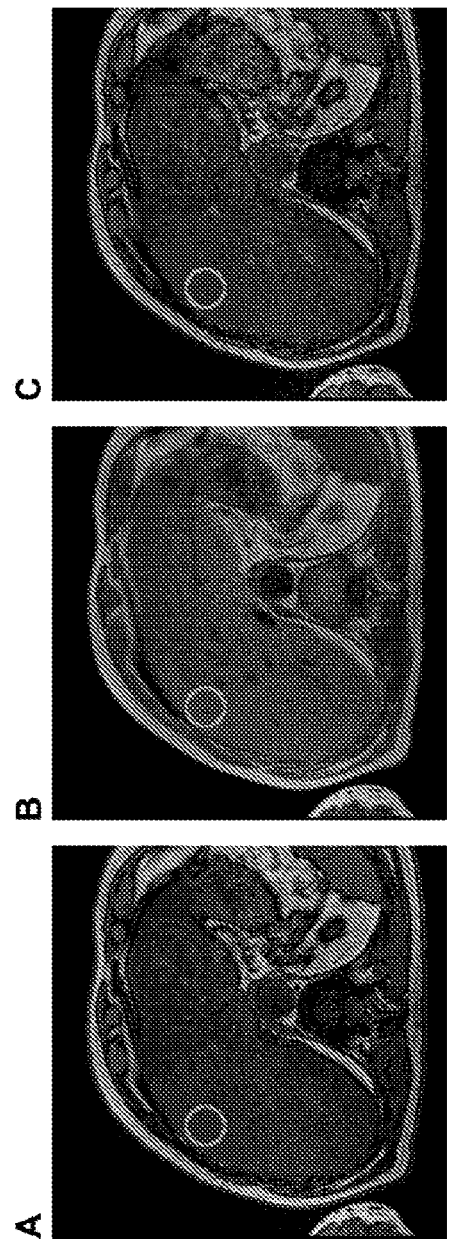
FIG. 5 shows axial magnetic resonance images of a patient with a typical region of interest (solid circle) used for liver fat volume fraction analysis at echo time TE1, TE2 and TE3.

A single analyst, blinded to the identity and medical histories of the subjects, reviewed and processed all images using ImageJ 1.42 (NIH, USA). On each of the three slices a circular region of interest (ROI) about 580 mm2 was delineated within the right lobe of the liver, avoiding large intrahepatic vessels and any obvious motion-affected regions (FIG. 5). The average image intensities within the ROIs, for all three echoes and slices, were used to calculate the value, a.

The parameter α in the liver ROI was calculated for each slice using the equation (1) above.

Statistical Analysis

Descriptive clinical and demographic characteristics were compared using Chi-squared analysis (for categorical data) or the Student's t test (for continuous parametric data). The histopathological fat measurements and the computed a values were tested for normality using the Komolgorov-Smirnov test. Non-Gaussian distributions were summarised by their median value and range, and group differences compared using the non-parametric Mann-Whitney test. For non-Gaussian distributions the 95% prediction interval was calculated on the log-transformed data. Comparisons between techniques were assessed using Pearson's correlation coefficient. The performance of the MRI technique for predicting the histologically assessed fat grades was assessed using receiver operating characteristic (ROC) curve analysis. The area under the ROC curve (AUROCC) was used to assess the diagnostic performance of the MRI method against the biopsy observations. The thresholds of a were identified by the cut-off that produced the highest combined sum of sensitivity and specificity for distinguishing histological fat scores above and below the standard thresholds. Two ROC curve analyses were performed. The first analysis used the NASH histological scoring system cut-off values of ≥5%, ≥33%, and ≥66% liver fat (2), as determined by the visual estimation of the histopathologist, to define the diagnostic groups above and below the three cut-offs. A second ROC curve analysis used cut-offs in HIS-MORPH percentages of ≥1.42%, >3.86%, and >6.75%. These morphometric cut-offs were derived from the regression line of HIS-VIS and HIS-MORPH using the visual histopathologist cut-offs of 5%, 33% and 66% as input into the regression equation. A p value less than 0.05 was considered statistically significant.

(B) Results
Demographic and Clinical Data

Figure 6:
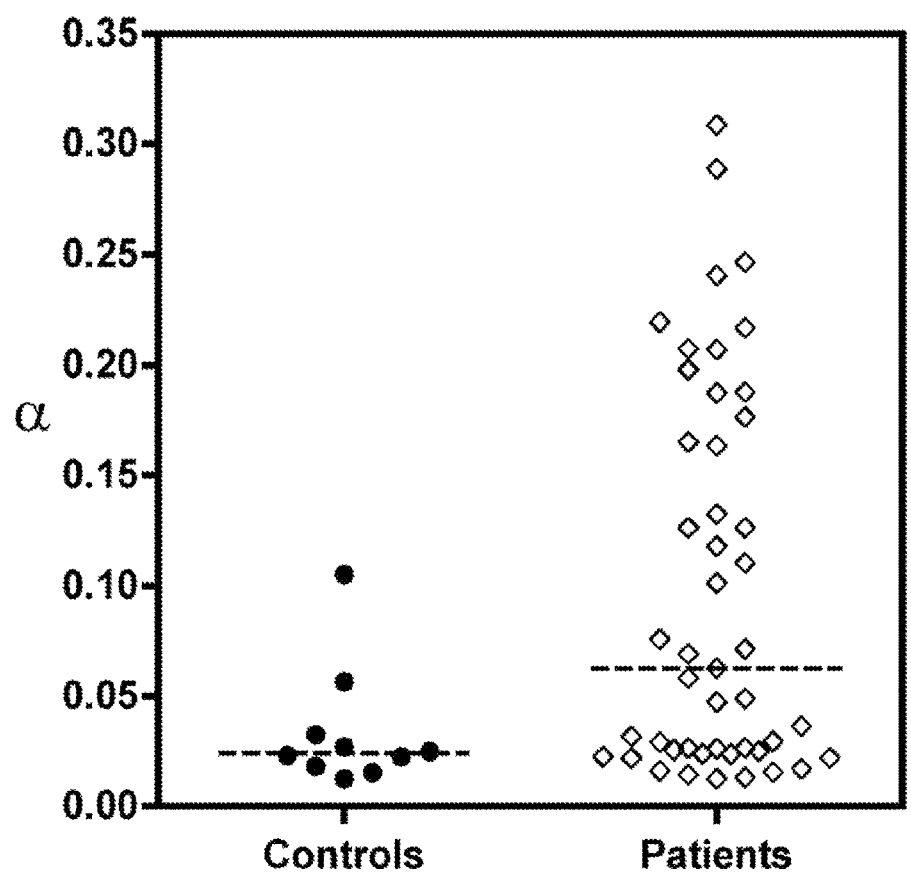
FIG. 6 is a plot of MRI derived α values for control and patient groups in the example with dashed horizontal line shows the median value for each group.

The control subjects were younger and had lower BMIs than the patients (Table 1). Histopathological fat estimates and MRI α values were not normally distributed. The median liver fat level of all patients was 5% (range 0 to 95%) from HIS-VIS and 1.08% (range 0.22 to 12.09%) from HIS-MORPH. The median value of α for the control subjects (0.024, range 0.0126 to 0.1051) was significantly lower compared to the patients (0.063, range 0.0125 to 0.3085, p=0.0205) (FIG. 6). The 95% prediction interval of a for the control subjects was 0.008 to 0.094. This prediction interval can be viewed as an estimate of the reference range of MRI α values for healthy subjects without liver problems.

Performance of MRI for Predicting Histological Fat Levels
The ROC curve analyses are summarised in Table 2.

TABLE 2

Diagnostic Performance of MRI for Predicting Degree of Liver Steatosis Observed in Biopsy Histological Section.

| Cut-off | MRI Cut off Value (α) | n | AUROCC | p value | Sensitivity | 95% CI | Specificity | 95% CI |
|---|---|---|---|---|---|---|---|---|
| Pathologist estimate - percentage of hepatocytes containing fat vacuoles | | | | | | | | |
| ≥5% (Brunt 0 vs 1-3) | >0.04164 | 25 | 0.9873 | <0.0001 | 100 | 86.28% to 100.0% | 90.9 | 70.84% to 98.88% |
| >33% (Brunt 0-1 vs 2-3) | >0.1221 | 13 | 0.9819 | <0.0001 | 100 | 75.29% to 100.0% | 88.24 | 72.55% to 96.70% |
| >66% (Brunt 0-2 vs 3) | >0.1707 | 10 | 0.9595 | <0.0001 | 90 | 55.5% to 99.75% | 91.89 | 78.09% to 98.3% |
| Morphometric image analysis - area of fat in biopsy sample | | | | | | | | |
| ≥1.42% | >0.07037 | 22 | 0.9867 | <0.0001 | 90.91 | 70.84% to 98.88% | 95.83 | 78.88% to 99.89% |

TABLE 2-continued

Diagnostic Performance of MRI for Predicting Degree of Liver
Steatosis Observed in Biopsy Histological Section.

| Cut-off | MRI Cut off Value ($\alpha$) | n | AUROCC | p value | Sensitivity | 95% CI | Specificity | 95% CI |
|---|---|---|---|---|---|---|---|---|
| >3.86% | >0.1141 | 15 | 0.9613 | <0.0001 | 93.33 | 68.05% to 99.83% | 87.10 | 70.17% to 96.37% |
| >6.75% | >0.1876 | 9 | 0.9610 | <0.0001 | 88.89 | 51.75% to 99.72% | 94.59 | 81.81% to 99.34% |

The analyses showed that the MRI $\alpha$ values had high sensitivity and specificity at all liver fat thresholds (Table 2). The areas under the ROC curves were marginally lower for two of the three comparisons defined by morphometric image analysis compared to the pathologist's visual estimate (Table 2). At the highest fat levels (>66% visual, 6.75% morphometric), the diagnostic performance of the MRI against the morphometric image analysis was slightly better than against the visual estimate.

Relationship Between MRI and Histology

As mentioned above, the relationship between $\alpha$ and the volume fraction of fat in the liver was not expected to be linear owing to both the difference in proton density between fat and the surrounding tissue and the difference in longitudinal relaxation time T1 between fat and the surrounding tissue.

As described above, the relationship between $\alpha$ and volume fraction (f) of fat in the liver is expected to be of the form described in equation (3) above.

Figure 7:
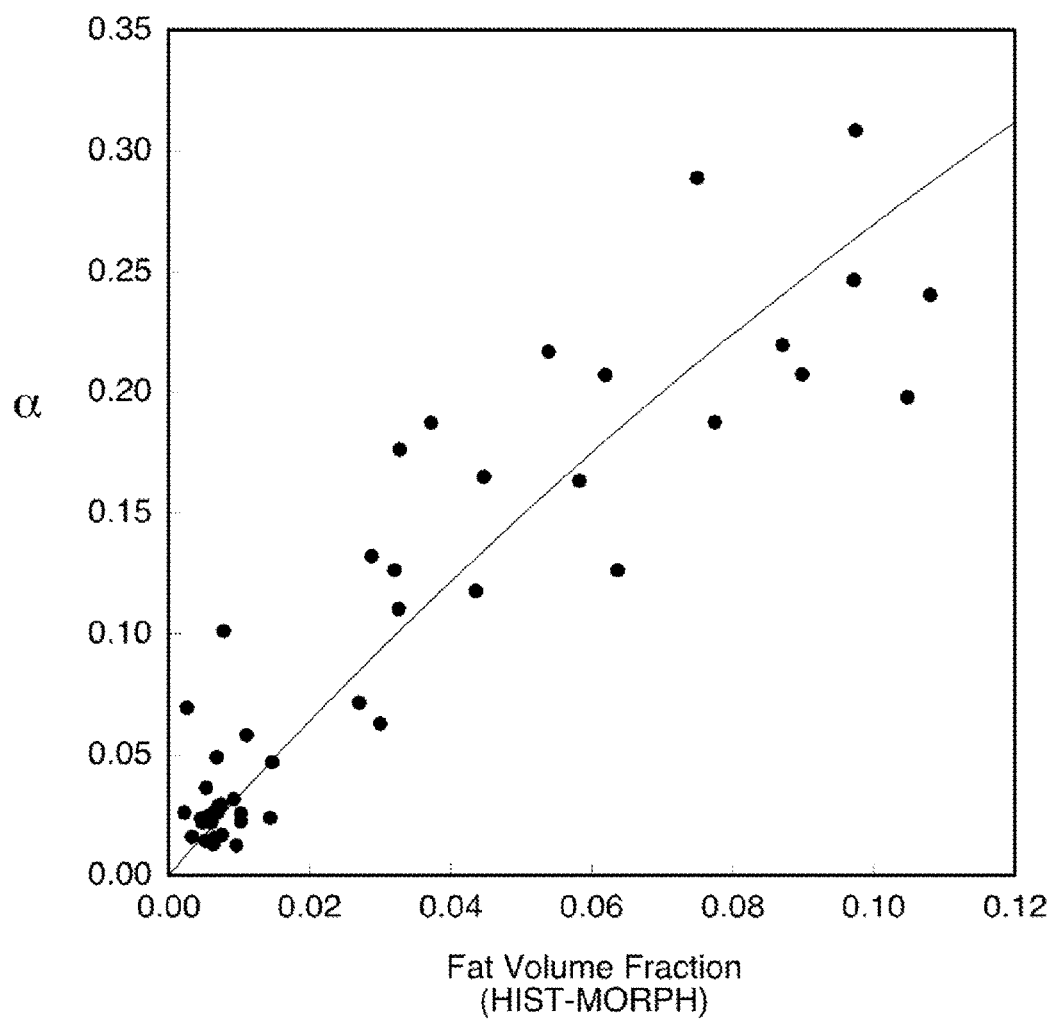
FIG. 7 is a plot of the MRI derived α value versus the fractional area of fat vacuoles in a histological section (HIST-MORPH) for an example of the present invention noting that the fractional area of fat vacuoles in a thin section is equivalent to volume fraction of fat: the solid line being a fit of equation 3 to the data.

Since the fat vacuoles are approximately spherical and the histological sections are thin compared to the size of the fat vacuoles, the percentage area of the histological section accounted for by fat vacuoles (HIS-MORPH) will be equal to the volume fraction of fat in the liver tissue. FIG. 7 shows a fit of equation (3) to the $\alpha$ versus HIS-MORPH data. The coefficient of determination, r2, for this fit was 0.84 and the value of k determined from this fit was k=3.32 (to two decimal places) as described above in Example 1.

Figure 8:
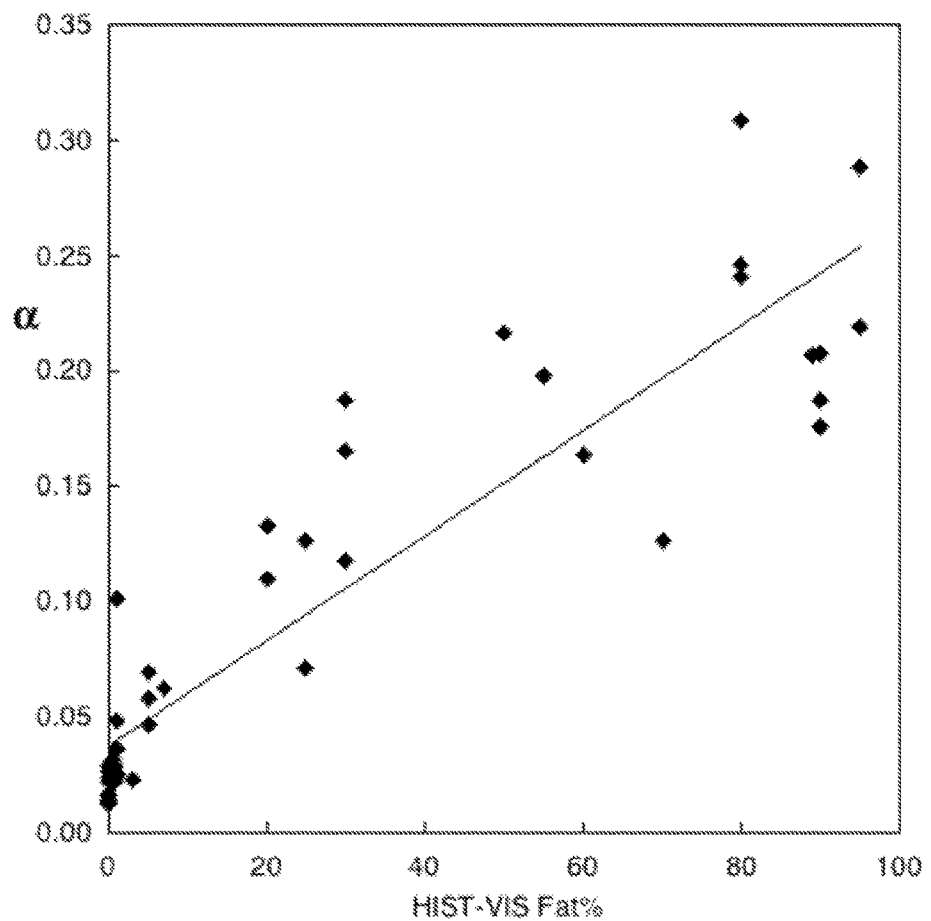
FIG. 8 is a plot of the MRI derived α value versus histopathologist's estimate of percentage of hepatocytes containing a fat vacuole (HIST-VIS) for an example of the present invention.
Figure 9:
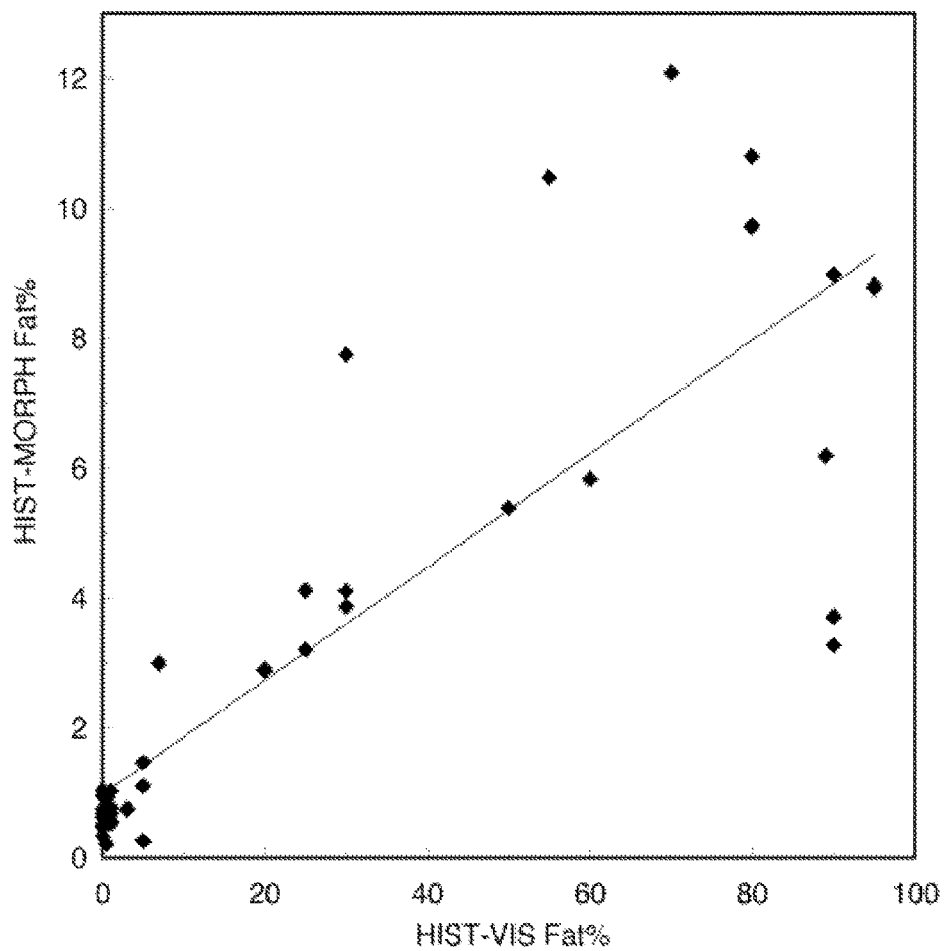
FIG. 9 is a plot of the percentage area of fat vacuoles in the histological section (HIST-MORPH) versus histopathologist's estimate of percentage of hepatocytes containing a fat vacuole (HIST-VIS) for an example of the present invention.

Scatter plots of histopathologist's visual estimates of hepatocyte fat involvement and the MRI $\alpha$ values and HIS-MORPH values are presented in FIGS. 8 and 9. The linear regression analysis showed that there were significant correlations between the pathologist's visual estimates of fat, the morphometric fat area and $\alpha$ from the MRI measurement (FIGS. 8 and 9).

Example 3B—Diagnostic Performance of a Rapid Magnetic Resonance

Imaging Method of Measuring Hepatic Steatosis

The study in Example 3A was continued to include more patients and the updated information is provided herein as Example 3B. To the extent there are any inconsistencies between Example 3A and 3B the details in Example 3B is to take precedence.

(A) Materials/Methods

Subjects

Ten healthy controls and 65 patients were enrolled in the study. Written informed consent was obtained from each subject and the study protocol conformed to the ethical guidelines of the 1975 Declaration of Helsinki as reflected in approval by the Fremantle Hospital Human Research Ethics Committee and the Sir Charles Gairdner Hospital Human Research Ethics Committee. The patients were recruited from the hepatology outpatient clinics at Fremantle and Sir Charles Gairdner Hospitals, Western Australia. The patient inclusion criteria were: age between 18 and 75 years and written informed consent. Control subjects were not biopsied and required a body mass index (BMI) less than 25 and no history of liver disease. The control subjects were included to provide a baseline of normal liver fat levels as measured by this MRI technique. Exclusion criteria were: contraindications for MRI, pregnancy or lactation. One patient was also excluded after their history indicated fluctuations in weight and alcohol consumption during the study period. An additional five cases were excluded for incorrect MRI acquisition or unavailability of images for morphometric analysis leaving 59 patients that entered the study. The details of the cohorts are shown in Table 3.

TABLE 3

Study Cohort Details

| Characteristics | Controls | Chronic Liver Disease Patients | Patients with MRI and Morphometry |
|---|---|---|---|
| N | 10 | 65 | 59 |
| Gender (F/M) | 3/7 | 31/34 | 29/30 |
| Age (years), median (range) | 33.5 (24-47) | 56 (20-72)* | 56 (20-72)* |
| BMI (kg/m$^2$), mean ± st. dev. | 22.55 ± 1.77 | 29.00 ± 5.11# | 28.92 ± 5.17# |
| LIC (mg/g), median (range) | 1.2 (0.4-1.8) | 0.9 (0.3-4.8) | 0.9 (0.3-4.4) |
| Diagnosis | | | |
| AIH | | 3 | 3 |
| ALD | | 3 | 2 |
| HBV-HCV | | 18 | 16 |
| NAFLD | | 11 | 10 |
| NASH | | 19 | 17 |
| NORM | | 3 | 3 |
| PSC | | 4 | 4 |
| OTHER | | 4 | 4 |

*Significantly different from controls, p < 0.05 Mann-Whitney test
Significantly different from controls, p < 0.05 unpaired t-test
Abbreviations:
AIH, autoimmune hepatitis;
ALD, alcoholic liver disease;
BMI, body mass index;
HBV-HCV, viral hepatitis B/C;
LIC, liver iron concentration;
MRI, magnetic resonance imaging;
NAFLD, non-alcoholic fatty liver disease;
NASH, nonalcoholic steatohepatitis;
NORM, normal;
PSC, primary sclerosing cholangitis.

Liver Histology and Quantification of Liver Fat

The patients underwent percutaneous liver biopsy with ultrasound guidance as part of their routine clinical management. Each liver biopsy specimen was reviewed by an experienced hepatopathologist, blinded to the patient's identity and MRI data, who visually estimated the percentage of hepatocytes containing fat on a continuous scale between 0% and 100% (HIS-VIS). The METAVIR scoring system was used to stage the amount of fibrosis.

Computer Assisted Morphometric Image Analysis of Liver Fat Area

The fraction of vesicular fat vacuoles in Masson's trichrome stained histological sections was assessed by computer assisted morphometric image analysis. Histological sections of the biopsies were scanned in colour using an Aperio Scanscope XT (Aperio Technologies, Inc., California, USA) automated slide scanner and ImageScope software. Using ImageJ 1.42 (NIH, USA) software, the fat vacuoles were automatically identified and areas measured in a multi-stage process using thresholding, size, and circularity criteria. Fat vacuoles, holes, tears or vessels in the biopsy section appear as high intensity (white) areas (FIG. 4A). These high intensity regions were automatically segmented by applying a threshold intensity of 220 (out of 256) on the green image band, which on inspection provided the best contrast between fat vacuoles and liver parenchyma. The threshold image was converted into a binary image such that the fat vacuoles and any other high intensity regions were given a value of 255 and non-fat tissue a value of 0 (FIG. 4B). The fat vacuoles were then automatically identified and delineated using the Analyze Particles tool in ImageJ with a circularity index between 0.5 and 1 and a size threshold between 100 and 10000 pixels (equivalent to diameters from 5.6 to 56 µm). The circularity index ranges from 0 (infinitely elongated polygon) to 1 (perfect circle) and is defined as $(4\pi \times Area)/Perimeter^2$.

The criteria for thresholding intensity, size, and circularity were established by inspection of the results of different thresholds, sizes and circularities on the effective simultaneous exclusion of large vessels, ducts or other large areas of high intensity and inclusion of fat vacuoles. The analysis produced the size and circularity of each individual fat vacuole and the total area of all the fat vacuoles within the threshold ranges. To compute the total area of the biopsy sample, the binary image was reversed and the Fill Holes tool used to produce a biopsy image without holes. The total area of the biopsy sample was measured and the areal fat fraction (HIS-MORPH) computed from the ratio of fat area to total biopsy tissue area.

MRI

Data Acquisition

All MRI measurements were made on Siemens 1.5 T Avanto scanners (Siemens Medical Systems, Erlangen, Germany) at Fremantle Hospital, St John of God Murdoch Hospital, and Hollywood Private Hospital, Western Australia. The median time between biopsy and MRI was 58 days. Phased-array torso coils were centred over the liver of the subjects. MRI acquisition comprised an opposed-phase, in-phase, opposed-phase gradient echo sequence (TEs 2.38, 4.76, 7.14 ms, TR 88 ms, 1 excitation, flip angle 70 degrees, bandwidth 500 Hz). Data from three axial slices, positioned through the widest part of the liver, were acquired in a single breath-hold. The slice thickness was 4 mm and the matrix was 256×256 with a field of view 300×300 mm. Liver iron concentrations (LIC) were measured using a validated non-invasive MRI method (FerriScan®).

Image Processing

A single analyst, blinded to the identity and medical histories of the subjects, reviewed and processed all images using ImageJ 1.42 (NIH, USA). On each of the three slices a circular region of interest (ROI) about 580 mm² was delineated within the right lobe of the liver, avoiding large intrahepatic vessels and any obvious motion-affected regions (FIG. 5). The average image intensities within the ROIs, for all three echoes and slices, were used to calculate a parameter, a, (see Eqn. 1 above).

Statistical Analysis

Descriptive clinical and demographic characteristics were compared using Chi-squared analysis (for categorical data), the Student's t test (for continuous parametric data), or the Mann-Whitney test (for non-parametric data). Data were tested for normality using the Komolgorov-Smirnov test. Non-Gaussian distributions were summarised by their median value and range. For non-Gaussian distributions the 95% prediction interval was calculated on the log-transformed data. Relationships between continuous parameters were assessed using the coefficient of determination ($r^2$). The performance of the MRI technique for predicting the histologically measured fat grades was assessed using receiver operating characteristic (ROC) curve analysis. The area under the ROC curve (AUC) was used to assess the diagnostic performance of the MRI method against the biopsy observations. The thresholds of a were identified by the cut-off that produced the highest combined sum of sensitivity and specificity for distinguishing histological fat scores above and below the standard thresholds. Two ROC curve analyses were performed. The first analysis used the NASH CRN histological scoring system cut-off values of ≥5%, >33%, and >66% liver fat, as determined by the visual estimation of the hepatopathologist, to define the diagnostic groups above and below the three cut-offs. A second ROC curve analysis used cut-offs in HIS-MORPH fractions of ≥0.014, >0.043, and >0.077. These morphometric cut-offs were derived from the regression line of HIS-MORPH against HIS-VIS using the visual histopathologist cut-offs of 5%, 33% and 66% as input into the regression equation. A p value less than 0.05 was considered statistically significant.

(B) Results

Demographic and Clinical Data

The control subjects were younger and had lower BMIs than the patients (Table 3). BMI values were normally distributed. Thirty-two patients had no/mild fibrosis (METAVIR 0 or 1) and 27 patients had moderate/severe fibrosis (METAVIR 2, 3 or 4). Five patients had liver iron concentration levels above the normal maximum level of 1.8 mg[Fe]/g dry tissue. The median liver fat level of the 59 patients was 5% (range 0 to 98%) from HIS-VIS and 0.029 (range 0.002 to 0.216) from HIS-MORPH. The median value of α for the control subjects (0.024, range 0.013 to 0.105) was significantly lower compared with the patients (0.072, range 0.01 to 0.41, p=0.012). The 95% prediction interval of α for the control subjects was 0.008 to 0.094. This prediction interval can be viewed as an estimate of the reference range of MRI α values for healthy subjects without liver problems. Interestingly, one of the ten control subjects without any recognised liver condition was outside this reference range.

Performance of MRI for Predicting Histological Fat Levels

The ROC curve analyses are summarised in Tables 4 and 5.

TABLE 4

Analysis of the area under the receiver operating characteristic curve using the histopathologists visual estimate of fat in the histological sections.

| Cut-off | MRI Cut off Value (α) | AUC | p value | Sensitivity | 95% CI | Specificity | 95% CI |
|---|---|---|---|---|---|---|---|
| ≥5% (Grade 0 vs 1-3)* | >0.067 | 0.9615 | <0.0001 | 90.91 | 75.67 to 98.08 | 96.15 | 80.36 to 99.90 |
| >33% (Grade 0-1 vs 2-3)* | >0.135 | 0.9928 | <0.0001 | 100.0 | 85.18 to 100.0 | 97.22 | 85.47 to 99.93 |
| >66% (Grade 0-2 vs 3)* | >0.171 | 0.9724 | <0.0001 | 100.0 | 79.41 to 100.0 | 88.37 | 74.92 to 96.11 |

*Cut-offs are defined according to the NASH CRN grading system.
Abbreviations: AUC, Area under receiver operating characteristic curve; MRI, magnetic resonance imaging

TABLE 5

Analysis of the area under the receiver operating characteristic curve using the morphometric image analysis estimate of fat in the histological sections.

| Cut-off | MRI Cut off Value (α) | AUC | p value | Sensitivity | 95% CI | Specificity | 95% CI |
|---|---|---|---|---|---|---|---|
| ≥0.014 | >0.060 | 0.9639 | <0.0001 | 90.91 | 75.67 to 98.08 | 96.15 | 80.36 to 99.90 |
| >0.043 | >0.141 | 0.9925 | <0.0001 | 100.0 | 83.89 to 100.0 | 92.11 | 78.62 to 98.34 |
| >0.077 | >0.188 | 0.9869 | <0.0001 | 100.0 | 79.41 to 100.0 | 93.02 | 80.94 to 98.54 |

Abbreviations: AUC, Area under receiver operating characteristic curve; MRI, magnetic resonance imaging The analyses showed that the MRI α values had high AUCs, sensitivities and specificities at all three liver fat thresholds (Table 4, 5). Based on the ROC curve analysis, the clinically relevant NASH CRN steatosis grade boundaries of 5%, 33% and 66% correspond to MRI α values of 0.067, 0.135, and 0.171, respectively (Table 4). There were no significant differences between the AUC's from morphometric image analysis compared with the pathologist's visual estimate (Table 4, 5).

Relationship Between MRI and Histology

The relationship between α and the volume fraction of fat in the liver is not expected to be linear owing to both the difference in proton density between fat and the surrounding tissue and the difference in T1 (the MRI related parameter known as the longitudinal relaxation time constant) between fat and the surrounding tissue. The relationship between α and volume fraction (f) of fat in the liver is expected to be of the form of equation 3 above.

Figure 11:
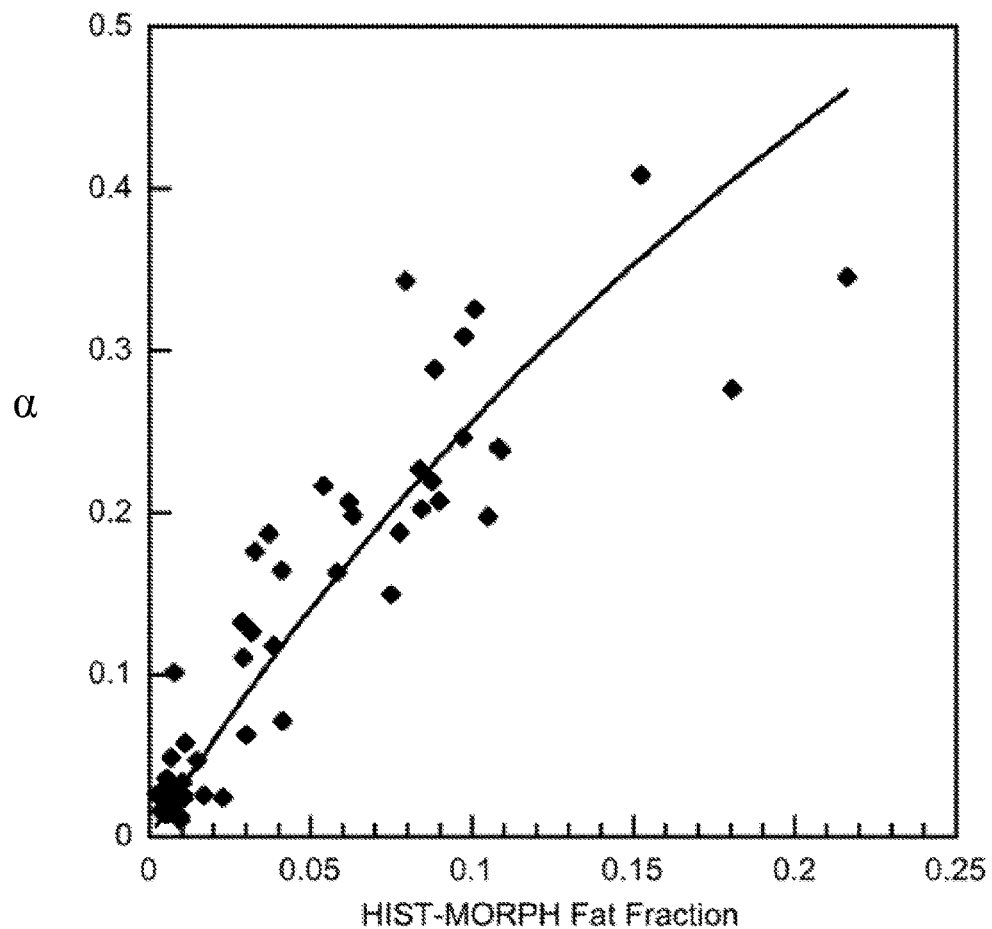
FIG. 11 is a plot of the MRI derived α value versus fractional area of fat vacuoles in the histological section (HIST-MORPH). The solid line is a fit of Equation 3 to the data ($r^2$=0.84)

FIG. 11 shows a fit of Equation 3 to the α versus HIS-MORPH data. The coefficient of determination, r2, for this fit was 0.84.

Figure 12:
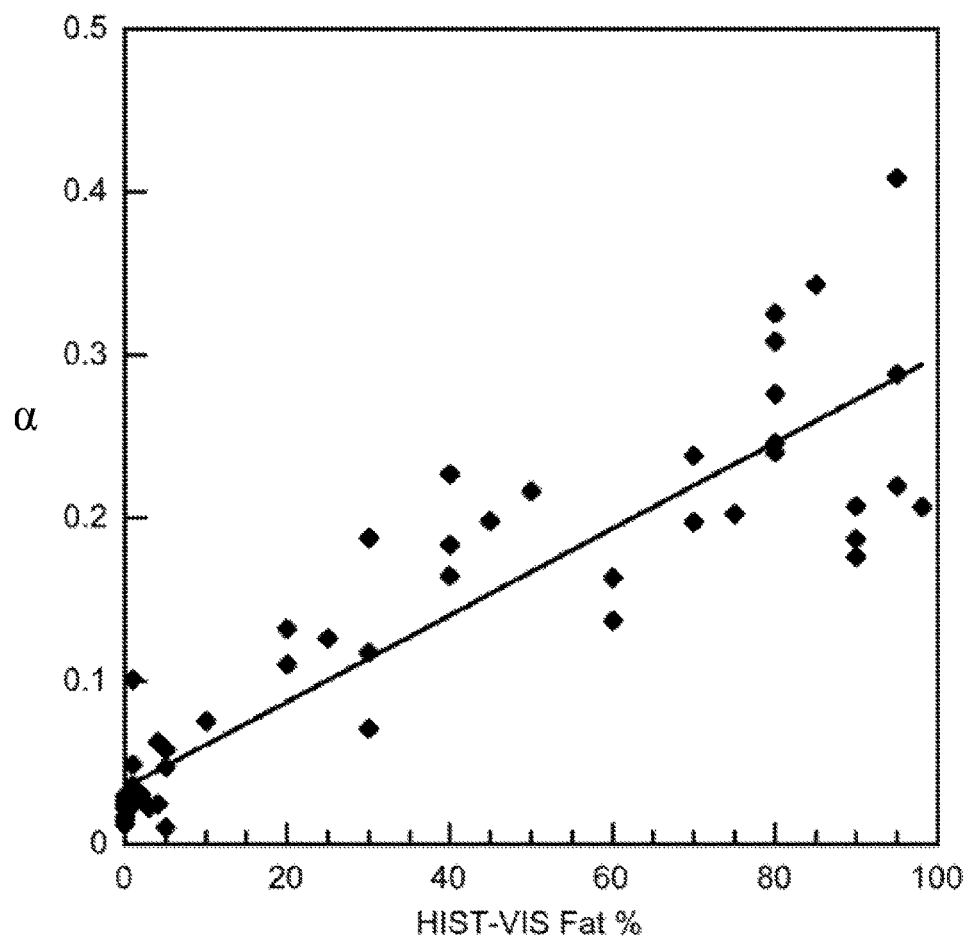
FIG. 12 is a plot of the MRI derived α value versus histopathologist's estimate of percentage of hepatocytes containing a fat vacuole (HIST-VIS). The solid line is the linear regression fit to the data ($r^2$=0.83).

Linear regression analysis showed that there were significant coefficients of determination between the pathologist's visual estimates of fat (HIST-VIS) and a from the MRI measurement (r2=0.83, FIG. 12) and between the pathologist's visual estimates of fat (HIST-VIS) and the morphometric fat fraction HIS-MORPH (r2=0.72).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. For example, other parameters for operation of the MRI scanner can be used: such as flip angles, repetition times, echo times, the number of slices taken, measured region-of-interest, and selection of different values of k as required. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims.

The invention claimed is:

1. A method for determining an estimate of fat within a volume of a subject comprising the steps of:
   a) generating a magnetic resonance image scan with a magnetic resonance image scanner that acquires the signal intensities of at least three echo signals emitted from a region of the volume, using a flip angle of 30°-70° or 70°-90°, and in response to an applied RF pulse, wherein the three echo signals are taken at a first opposing-phase echo time, a second opposing-phase echo time, and an in-phase echo time;
   b) determining a parameter α from the acquired signal intensities, a reflecting a fat signal fraction within the volume; and
   c) determining a fat volume fraction, f from the parameter α, using equation (3)

$$\alpha = \frac{kf}{(1 + kf - f)} \qquad \text{(Equation 3)}$$

where k is a constant greater than 1 and f is less than 1.

2. A method according to claim 1 and further comprising selecting k when the rate of change of α with respect to the fat volume fraction, f, is maximized to optimize the rate of change of α with respect to the fat volume fraction.

3. A method according to claim 2 wherein k is less than or equal to 10.

4. A method according to claim 1 wherein said scan was generated using a flip angle of 30°-70°.

5. A method according to claim 1 wherein a is determined by means of equation (1):

$$\alpha = \frac{IP - OP1\left[\exp\left(\frac{TE1 - TE2}{T2^*}\right)\right]}{2IP}$$

where T2* is determined according to equation (2):

$$T2^* = \frac{(TE3 - TE1)}{\ln\left(\frac{OP1}{OP2}\right)}$$

and where TE1 is the first opposing-phase echo time, TE2 the in-phase echo time, TE3 the second opposing-phase echo time, OP1 and OP2 are the signal intensities measured at the first and second opposing-phase echo times, TE1 and TE3, and IP is the signal intensity measured at the in-phase echo time.

6. A method according to claim 1 further comprising the step of correcting the signal intensities for background noise.

7. A method according to claim 6 wherein the signal intensities are corrected by subtracting the background noise signal intensities in quadrature.

8. A method according to claim 6 wherein the signal intensities are corrected for background noise by determining the parameter α by means of equation (1'):

$$\alpha = \frac{IP_T - OP1_T \left[\exp\left(\frac{TE1 - TE2}{T2^*}\right)\right]}{2IP_T}$$

where T2* is determined according to equation (2'):

$$T2^* = \frac{(TE3 - TE1)}{\ln\left(\frac{OP1_T}{OP2_T}\right)}$$

and $OP1_T$, $IP_T$ and $OP2_T$ are the true signal intensities in the absence of noise in regions-of-interest in the first opposed-phase, in-phase and second opposed-phase images, wherein the true signal intensity, $S_T$, is determined as follows:

$$S_T = \sqrt{S_M^2 - N_M^2}$$

where:
$S_T$ is the true signal intensity within the region-of-interest corrected for background noise levels, $S_M$ is the measured signal intensity within the region-of-interest in the magnitude MR image and $N_M$ is the measurement of the background noise levels in the magnitude image in an area free of image artefacts and structured noise.

9. A method according to claim 6 wherein the background noise signal is determined by one or more of (i) the statistical mean of the signal intensities within the background region-of-interest of the magnitude image; (ii) the statistical mean plus an offset of one standard deviation of the background noise intensity levels; (iii) the mean of a probability density function fitted to the distribution of the signal intensities within the background region-of-interest; (iv) the mean plus one standard deviation of a probability density function fitted to the distribution of the background noise intensity levels.

10. A method according to claim 9 wherein the probability density function is selected from the group comprising: a Gaussian distribution, a Rician distribution and a Poisson distribution.

11. A method according to claim 1 wherein a is determined as the average of three consecutive axial image slices along an axis.

12. A method according to claim 1 wherein the volume of the subject comprises an organ, or part of an organ.

13. A method according to claim 12 wherein the organ is a liver, kidney, or pancreas.

14. A method according to claim 1, wherein a computer program is used to determine the parameter α and
determine the fat volume fraction, f, from the parameter α, using equation (3)

$$\alpha = \frac{kf}{(1 + kf - f)} \quad \text{(Equation 3)}$$

where k is a constant greater than 1 and f is less than 1.

15. A method according to claim 1, which comprises using a computer system comprising: a processor, and a non-transitory computer-readable medium comprising instructions stored thereon, that when executed by the processor, performs steps b) and c).

16. A system for determining an estimate of fat within a volume of a subject, the system comprising: a magnetic resonance imaging scanner that acquires signal intensities of at least three echo signals emitted from a region of the volume, using a flip angle of 30°-70° or 70°-90°, and in response to an applied RF pulse, wherein the three echo signals are taken at a first opposing-phase echo time, a second opposing-phase echo time, and an in-phase echo time; and a computing device comprising a processor, and a non-transitory computer-readable medium comprising instructions stored thereon, that when executed by the processor, performs the steps of:
  a) generating a magnetic resonance image scan with the magnetic resonance image scanner, and determining, from the magnetic resonance image scan, a parameter α from the acquired signal intensities of at least three echo signals emitted from a region of the volume, using a flip angle of 30°-70° or 70°-90°, and in response to an applied RF pulse, a reflecting a fat signal fraction within the volume, wherein the three echo signals are taken at a first opposing-phase echo time, a second opposing-phase echo time and an in-phase echo time; and
  b) determining a fat volume fraction, f from the parameter α, using equation (3)

$$\alpha = \frac{kf}{(1 + kf - f)} \quad \text{(Equation 3)}$$

where k is a constant greater than 1 and f is less than 1.

* * * * *